(12) United States Patent
Harder et al.

(10) Patent No.: US 9,063,205 B2
(45) Date of Patent: Jun. 23, 2015

(54) METHOD AND MAGNETIC RESONANCE APPARATUS FOR IMAGE DATA ACQUISITION

(75) Inventors: Martin Harder, Nuremberg (DE); Dominik Paul, Bubenreuth (DE); Raphael Schwarz, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 159 days.

(21) Appl. No.: 13/554,247

(22) Filed: Jul. 20, 2012

(65) Prior Publication Data

US 2013/0023754 A1 Jan. 24, 2013

(30) Foreign Application Priority Data

Jul. 20, 2011 (DE) .................. 10 2011 079 503

(51) Int. Cl.
  *A61B 5/055* (2006.01)
  *G01R 33/54* (2006.01)
(52) U.S. Cl.
  CPC ............ *G01R 33/543* (2013.01); *A61B 5/0555* (2013.01)
(58) Field of Classification Search
  CPC ..... A61B 5/0555; G01R 33/543; G01R 33/48
  See application file for complete search history.

(56) References Cited

U.S. PATENT DOCUMENTS

| | | | | |
|---|---|---|---|---|
| 4,875,486 A | * | 10/1989 | Rapoport et al. | 600/415 |
| 6,262,575 B1 | | 7/2001 | Bruder et al. | |
| 7,908,690 B2 | * | 3/2011 | Luginbuhl et al. | 5/601 |
| 2008/0231275 A1 | * | 9/2008 | Jattke et al. | 324/309 |
| 2010/0158338 A1 | | 6/2010 | Harder et al. | |
| 2010/0207627 A1 | * | 8/2010 | Hughes et al. | 324/309 |

* cited by examiner

*Primary Examiner* — Ruth S Smith
(74) *Attorney, Agent, or Firm* — Schiff Hardin LLP

(57) ABSTRACT

In a magnetic resonance method and apparatus wherein the magnetic resonance device has a movable patient bed, in a first overview measurement, a first image data record of a patient is acquired, and patient information and/or information of a treatment region of a patient is/are determined from the acquired first image data record. In a second overview measurement, dependent on the patient information and/or on the positioning information of the treatment region of the first image data record, a second image data record is acquired. In a planning step a layer planning for the image data acquisition is implemented from the acquired second image data record. Image data for a medical and/or diagnostic issue and/or examination are recorded. The first image data record of the first overview measurement is recorded with a lower spatial resolution than a spatial resolution of the second image data record of the second overview measurement.

4 Claims, 3 Drawing Sheets

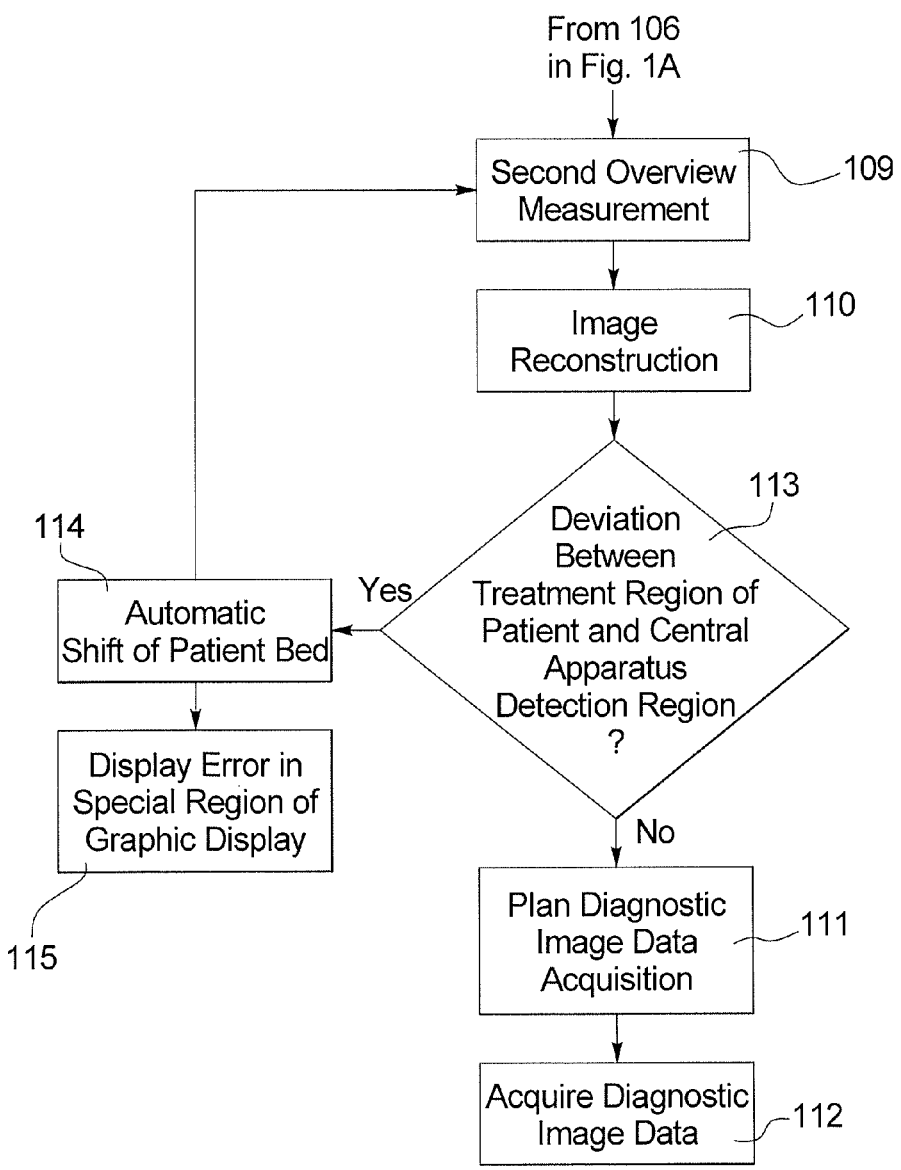

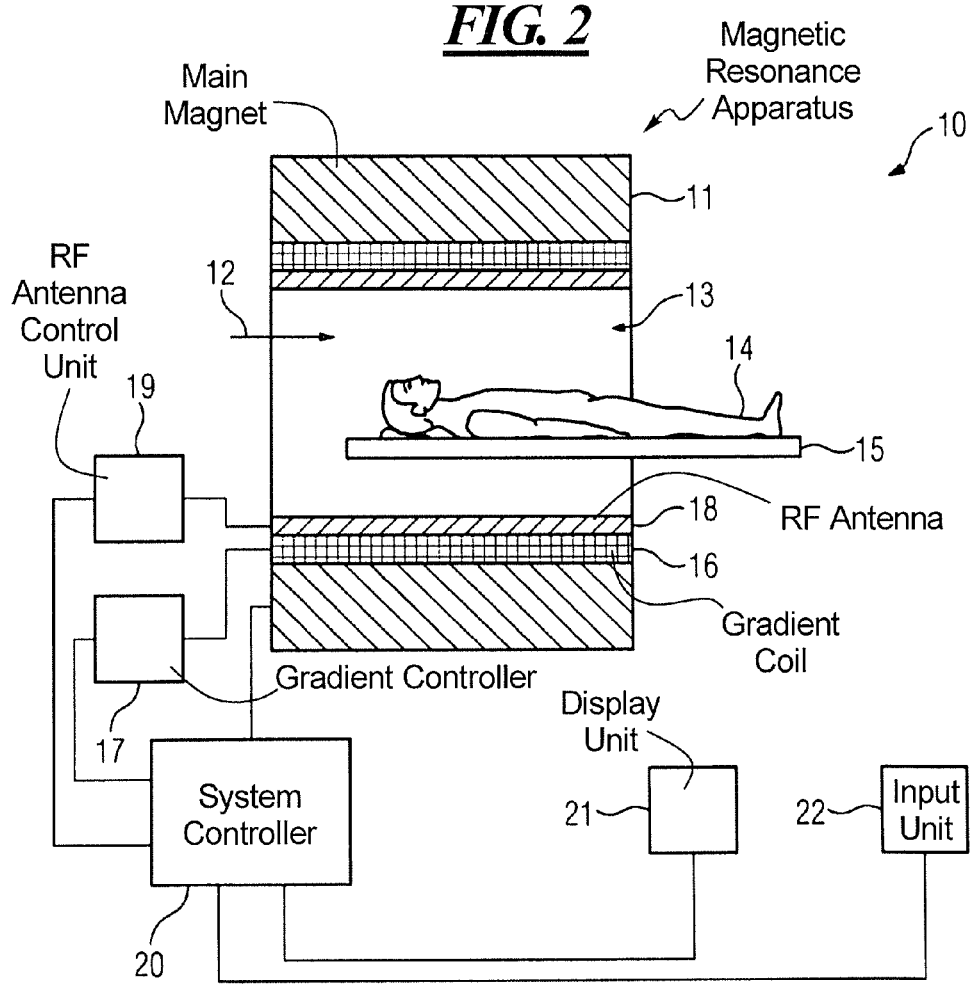

METHOD AND MAGNETIC RESONANCE APPARATUS FOR IMAGE DATA ACQUISITION

BACKGROUND OF THE INVENTION

1. Field of the Invention

The present invention relates to a method for image data acquisition by means of a magnetic resonance apparatus that has a movable patient bed.

2. Description of the Prior Art

Raw data from multiple layers of a treatment region of a patient are acquired and/or recorded by means of a magnetic resonance apparatus for a magnetic resonance examination in which image data for a medical and/or diagnostic issue and/or examination are obtained from the raw data. An exact and/or correct setting of these layers with regard to layer geometry, such as for example a position and/or an orientation and/or thickness of the layer can be performed on the magnetic resonance apparatus by experienced users via a user interface, but this procedure is time consuming and extremely difficult.

In addition, a method is known in which case planning of layer geometry can be implemented at least partially automatically for a particular diagnostic question. In this method, image data are recorded in a planning step and parameters are determined from the image data for a position of the patient and/or of a treatment region. With the help of these parameters a planning of the image data acquisition occurs. However, this method has the disadvantage that coordinate determination of the treatment region and the layer planning are determined from the same data record or from different data records which however exhibit an identical spatial resolution. This has disadvantageous effects on the method, in particular in the case of an incorrect positioning of patients within the imaging region of the magnetic resonance apparatus, since the recording and evaluation of the image data records for the planning of the layer geometry are very time-consuming for the diagnostic question and, in the case of an incorrect positioning, an image data record must be recorded again.

SUMMARY OF THE INVENTION

An object of the present invention is to provide a method for image data acquisition in which rapid position information and/or patient information are available for planning prior to a scheduling of a magnetic resonance measurement (data acquisition procedure), in which image data are recorded for a medical and/or diagnostic question and/or examination.

The invention proceeds from a method for image data acquisition by operation of a magnetic resonance apparatus that has a movable patient bed, wherein, in a first overview measurement, a first image data record of a patient is acquired, and patient information and/or positioning information of a treatment region of the patient is/are determined from the acquired first image data record. In a second overview measurement dependent on the patient information and/or positioning information of the treatment region of the first image data record, a second image data record is acquired. In a planning step, a layer planning for the image data acquisition is implemented from the acquired second image data record. Image data about a medical and/or diagnostic issue and/or question on are recorded.

Preferably the first image data record of the first overview measurement is acquired with a lower spatial resolution than the spatial resolution of the second image data record of the second overview measurement. As a result, the data acquisition time and/or evaluation time for the first overview measurement can be significantly shortened with respect to the measuring time and/or evaluation time for the second overview measurement. In addition, advantageously a rapid recording can be achieved of a position of the treatment region and/or of a position of the patient within an examination region and/or detection region of the magnetic resonance apparatus. A measuring and evaluation time for the second overview measurement and an evaluation of the second image data record amounts to about 35 s to 90 s. A measuring and evaluation time for the first overview measurement and an evaluation of the first image data record takes a maximum of 10 s and preferably a maximum of 5 s. Preferably a number of layers essentially amount to one layer for the entire first image data record, so that the patient information and/or positioning information of the treatment region of the patient can be provided particularly expeditiously. In the case of especially difficult body regions of the patient the number of layers can also range from two to a maximum of three layers. The low spatial resolution of the first image data record in the first overview measurement is sufficient for the recording of the patient information and/or positioning information of the treatment region, but an exact layer planning can be carried out only by means of the second image data record of the second overview measurement with the higher spatial resolution. Preferably the spatial resolution in the second image data record is greater by a factor of 2, preferably by at least a factor of 5, than the spatial resolution in the first image data record.

In this connection, patient information in particular means information about a positioning and/or a position of the patient relative to and/or on the patient bed, such as for example a prone position or a supine position of the patient on the patient bed. The treatment region is preferably formed of a region of the patient which is arranged within a detection region for a magnetic resonance examination. In addition, positioning information of a treatment region means in particular position information for the treatment region, for example whether said region is arranged within a detection region or a field of view (FOV) of the magnetic resonance apparatus. The layer planning preferably occurs automatically by means of a controller of the magnetic resonance apparatus, wherein the controller determines information of layer geometry with the help of the second image data record. By means of the layer geometry the upcoming magnetic resonance examination can be adapted particularly exactly to a medical and/or diagnostic object under examination and in such a way the magnetic resonance examination for the recording of image data for the medical and/or diagnostic issue and/or examination can be carried out especially expeditiously.

In addition, preferably an automatic adjustment of the patient bed is implemented in dependence on the positioning information of the treatment region of the first image data record. Advantageously, the treatment region can be expeditiously arranged prior to the second overview measurement within a center, in particular an isocenter, of the detection region of the magnetic resonance apparatus and the second overview measurement can occur with the correctly positioned patient. In this context, an automatic adjustment of the patient bed means that the magnetic resonance apparatus has at least one controller and/or processing unit which, depending on the positioning information automatically calculates a new position of the patient within the recording region and with this a new position for the patient bed and automatically controls a movement of the patient bed.

In a further embodiment of the invention, after the automatic adjustment of the patient bed, a first overview measurement occurs again for renewed recording of a first image data record, as a result of which after the repositioning of the patient bed position information of the treatment region can be recorded again especially rapidly. Thus the position information can be checked once more with regard to an at least partial correspondence with the center, in particular with the isocenter, of the detection region of the magnetic resonance apparatus before a time-consuming planning of a layer geometry by means of the second overview measurement for the recording of image data for the medical and/or diagnostic issue and/or examination can occur.

In accordance with the invention, patient information and/or information of a treatment region of the patient can be determined once more with the use of the recorded second image data record of the second overview measurement. By means of the high spatial resolution of the measurement data an exact recording of the position of the patient, in particular of the treatment region, of the patient can be advantageously recorded for the final layer planning and in addition an imaging region of the second image data record can be focused on a region relevant for the magnetic resonance measurement. In addition, a time-consuming scanning of a large patient region by means of the second image data record can be dispensed with on the basis of the position determination from the first image data record.

Additionally, in the event of the detection of an incorrect position on the basis of the patient information and/or in the event of the detection of an incorrect position on the basis of the positioning information of the treatment region, an error message is emitted as an output to an operator. In this way an operator of the magnetic resonance apparatus or personnel carrying out the method can be informed quickly and easily of a possible incorrect position of the patient and/or an incorrect position of the treatment region. The incorrect position can be, for example, a prone position of the patient on the patient bed when a supine position of the patient on the patient bed would be required. An incorrect position in this context means a position outside of the center, in particular of the isocenter, of the detection region of the magnetic resonance apparatus and/or a position of the treatment region of the patient. For an effective magnetic resonance examination it is advantageous for the region of the patient to be examined to be located within the center, in particular of the isocenter, of the detection (imaging) region of the magnetic resonance apparatus in order to prevent undesirable distortions and/or artifacts which can arise in the case of an arrangement in a peripheral region of the isocenter.

In addition in accordance with the invention an extra graphic display area is generated for the display of the error message that is visibly represented for an operator on the display unit independently from the application of a display unit of the magnetic resonance apparatus. Thus a possible error message can always be displayed visibly for the operator and the operator can always be made aware of the error message independently from the currently running application, for example independently from imaging processing of magnetic resonance images. Preferably the graphic display area is generated by the controller immediately after the detection of the incorrect position, wherein the graphic display area is formed by a display window which is shown on a monitor and/or screen.

The invention also encompasses a magnetic resonance apparatus with a moveable patient bed and a controller for controlling image data acquisition by the apparatus in accordance with the above-described method.

BRIEF DESCRIPTION OF THE DRAWINGS

FIGS. 1A and 1B together form a flow chart of an exemplary embodiment of the inventive method for image data acquisition.

FIG. 2 is a schematic representation of an inventive magnetic resonance apparatus.

DESCRIPTION OF THE PREFERRED EMBODIMENTS

Figure 1A:
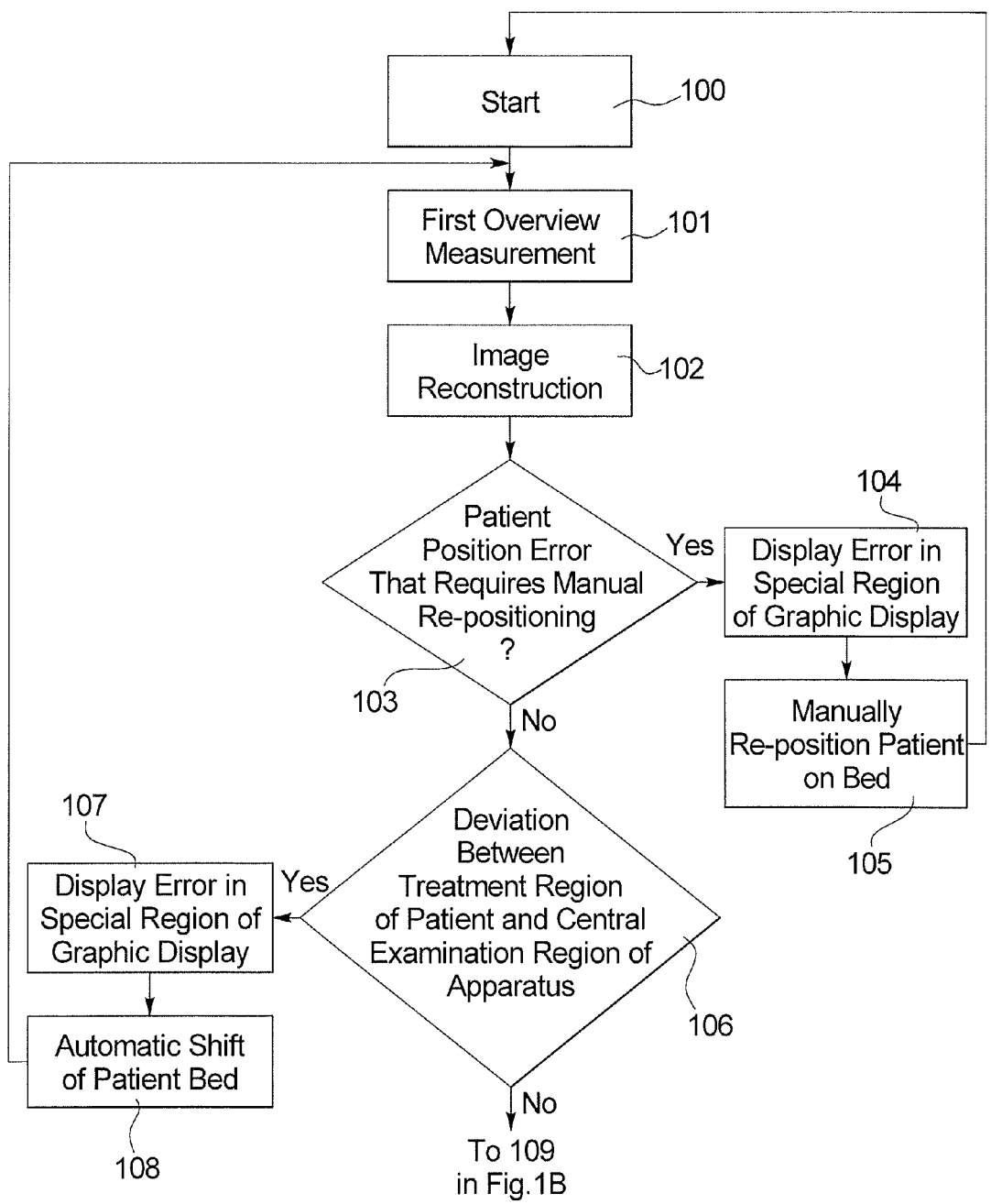

In FIG. 2 an inventive magnetic resonance apparatus 10 is shown. The magnetic resonance apparatus has a main magnet 11 for generation of a strong and constant basic magnet field 12. In addition, the magnetic resonance apparatus 10 has a cylindrical imaging region 13 for data acquisition from a patient 14, wherein the imaging region 13 is enclosed by the main magnet 11 in a circumferential direction. The patient 14 can be moved into the imaging region 13 by means of a patient bed 15 of the magnetic resonance apparatus 10. The patient bed 15 is arranged movably within the magnetic resonance apparatus 10.

The magnetic resonance apparatus 10 has a gradient coil 16 for a generation of magnetic field gradients, these gradients being used for spatial coding of the magnetic resonance signals during imaging. The gradient coil 16 is controlled by a gradient controller 17. In addition the magnetic resonance apparatus 10 has a radio-frequency (RF) antenna 18 and a radio-frequency antenna unit 19 for excitation of a polarization which ensues in the main magnetic field 12 generated by the main magnet 12. The radio-frequency antenna 18 is controlled by the radio-frequency antenna control unit 19 so as to irradiate radio-frequency magnetic resonance pulse sequences into an examination space volume that is essentially formed by the imaging region 13. As a result, the magnetization of nuclear spins in the patient 14 is deflected from its equilibrium position and resulting magnetic resonance signals are received by means of the radio-frequency antenna unit 19.

The magnetic resonance apparatus 10 has a system controller 20 formed by a processing unit for controlling the main magnet 11, the gradient controller 17 and for controlling the radio-frequency antenna unit 19. The processing unit centrally controls the magnetic resonance apparatus 10, for example the carrying out of a predetermined imaging gradient echo sequence. Control information such as, for example imaging parameters, as well as reconstructed magnetic resonance images can be displayed on a display unit 21, for example on at least one monitor, of the magnetic resonance apparatus 10 for an operator of the magnetic resonance apparatus 10. In addition, the magnetic resonance apparatus 10 has an input unit 22, by means of which information and/or parameters can be input by an operator during a measurement operation.

The shown magnetic resonance apparatus 10 can of course include further components as are used for magnetic resonance apparatuses. The basic operation of a magnetic resonance apparatus is known to those skilled in the art, so that a detailed description of the basic components is not necessary herein.

In FIGS. 1A and 1B an embodiment of the inventive method for image data acquisition by operation of the magnetic resonance apparatus 10 is shown. The method is caused to be executed by the system controller 20 of the magnetic resonance apparatus 10 and begins after a start signal 100 is manually entered by an operator, such as a member of the clinic staff running the magnetic resonance apparatus 10.

Otherwise, the method is implemented automatically by means of the system controller 20. To this end computer programs and additional software are stored on a memory unit of the controller 20 (not shown), by means of which a processor of the controller 20 (not shown) automatically controls and/or executes the method for image data acquisition.

In this method for image data acquisition a first image data record is recorded in a first overview measurement 101 by means of the magnetic resonance apparatus 10, controlled by the controller 20. For the recording of the first image data record it is as a rule sufficient to record only one layer of image data. By means of the image data of the first image data record in a first reconstruction step 102 the controller 20 determines patient information and position information of a treatment region of the patient 14. The first image data record encompasses a large spatial coverage that preferably extends to the entire detection region of the magnetic resonance apparatus, so that the position of the treatment region within the detection region of the magnetic resonance apparatus can be recorded.

The patient information can indicate the position of the patient 14 on the patient bed 15, such as for example a prone position or supine position of the patient 14. The position information of the treatment region of the patient 14 designates a region of the patient 14 which represents a relevant region of the patient 14 for a magnetic resonance measurement and which, for this purpose, should be located within the detection region of the magnetic resonance apparatus. In addition, in the first reconstruction step 102 the controller 20 compares the patient information and the position information determined by means of the first image data record with relevant data for the magnetic resonance measurement on the patient 14. The relevant data for the magnetic resonance measurement comprise a patient position within the imaging region 13 and/or with regard to the patient bed 15, for example a prone position or a supine position, and a position of the treatment region within the patient 14.

Furthermore, in the first overview measurement the treatment region can also be automatically detected and/or specified by the controller 20. For example, if the treatment region comprises a shoulder or a knee of the patient 14, in the first overview measurement the controller 20 can automatically make a selection as to which shoulder or which knee of the patient 14 is comprised by the treatment region. This automatic recording of the treatment region can occur with the aid of detected parameters of a local coil arranged around the treatment region within the first image data record.

If the comparison of the patient information with the relevant data in step 103 indicates an error with regard to the patient position, for example a deviation on the basis of an incorrect patient position of the patient on the patient bed 15 for the magnetic resonance measurement, the controller 20 generates an error message immediately after the presence of the error value 103 in an error output step 104 and displays said error message for the operator of the magnetic resonance apparatus 10 via the display unit 21. To this end, in addition the controller 20 generates a graphic display area especially for the error message which is formed by a window displayed on a user interface of a monitor in step 104. The graphic display area is visibly displayed on the display unit 21 for an operator independently from an application of a display unit 21 by having the window continually appear in the foreground and overlays additional graphically displayed applications on the display unit 21.

By means of the graphic display of the error value 103 detected by the controller 20 regarding the patient position this error value is directly pointed out to the operator. In the case of a deviation or of an existing error value 103 of the patient position the patient 14 must be manually positioned in a correct patient position on the patient bed 15 by the operator in a positioning step 105 and the method must be started again.

If the correct patient position is detected, the controller 20 performs a comparison and/or verification of the position information of the treatment region with the relevant data. If the controller 20 determines in step 106 that a deviation of the treatment region from a central detection region and/or the isocenter of the detection region exists, the controller 20 generates an error message in an error output step 107 and displays it via the display unit 21 for the operator of the magnetic resonance apparatus 10. To this end, analogous to the error output step 104 the controller 20 generates an extra graphic display area for the error message of error output step 107, wherein the graphic display area is formed by a window displayed on a user interface of the monitor. The graphic display area is displayed visibly for an operator on the display unit 21 independently from other items displayed at a display unit 21 in step 108, by having the window continually appear in the foreground and overlaying further graphically displayed items on the display unit 21.

By means of the graphic display of the error value in step 107 regarding the position of the treatment region detected by the controller 20 this error value is directly pointed out to the operator. In addition, if a deviation of the position information of the treatment region from the central detection region and/or the isocenter of the detection region of the apparatus is determined to exist in step 106, an automatic adjustment of the patient bed 15 is performed by the controller 20, so that the incorrect positioning of the patient 14 can be automatically eliminated by the controller 20. In this connection, with the use of the determined position information the controller 20 determines a position of the treatment region regarding the isocenter of the detection region. Subsequently, the controller 20 performs an automatic adjustment 108 of the position of the patient bed 15. In this connection the patient bed 15 has its position changed until a correspondence calculated by the controller 20 between the isocenter of the detection region and the treatment region of the patient 14 exists. To this end the magnetic resonance apparatus 10 can have a drive unit for a shifting of the patient bed 15, wherein the controller controls the drive unit.

After the shifting of the patient bed 15 automatically controlled by the controller 20, the controller 20 restarts the first overview measurement 101 and acquires a first image data record. From the first image data record patient information and/or position information about the treatment region is determined again. If there is not at least a partial correspondence between the treatment region and the isocenter of detection region from the new patient information and/or position information by means of having the treatment region overlay the isocenter of the detection region or by having the isocenter of the detection region overlay the treatment region, the steps of the method from the first overview measurement 101 to the adjustment 108 of the patient bed 15 can be repeated by the controller 20 so often that an at least partial correspondence exists between the treatment region and the isocenter of the detection region.

If the controller 20 does not detect a deviation in step 106 the controller 20 automatically starts a second overview measurement 109 for an acquisition of a second image data record. The image data of the second image data record exhibit a higher spatial resolution than a spatial resolution of the image data of the first image data record. Through the low spatial resolution of the image data of the first image data record an especially rapid recording of the patient information and of the position information can occur. For the layer planning of the magnetic resonance measurement, however, it is advantageous to have image data with a higher spatial resolution available in order to make possible an exact layer planning, for example a section though a relevant region of a joint of the patient 14 etc. In addition, the second image data record can image a smaller spatial region of the patient 14 than an imaging of a spatial region of the patient 14 in the first image data record.

By means of the image data of the second image data record, in a second reconstruction step 110 the controller 20 again determines patient information and position information about a treatment region of the patient 14. If there is a deviation between the treatment region of the patient 14 and the central region of the detection region (step 113), the controller 20 automatically performs a readjustment in the second overview measurement step 109 by shifting the patient bed 15 in step 114. Simultaneously an error message is output to the operator of the magnetic resonance apparatus 10 via the display unit 21 in step 115, by means of which the operator is informed about the deviation and/or the readjustment of the patient bed 15. To this end the, controller 20 generates a graphic display area especially for the error message, the display area being formed by a window, displayed on a user interface of the monitor. The graphic display area is likewise visibly displayed for an operator on the display unit 21, independently from other items displayed at the display unit, by having the window continually appear in the foreground and overlay further graphically displayed items on the display unit 21.

With the use of the image data of the second image data record in a planning step 111 an exact layer planning for the subsequent diagnostic magnetic resonance examination of the patient occurs. In the process, the controller 20 automatically performs the layer planning. In the process the controller 20 automatically determines a suitable layer geometry for the treatment region for the diagnostic magnetic resonance examination.

After the step of layer planning the diagnostic magnetic resonance examination 112 for the recording of image data for medical and/or diagnostic issues and/or examination occurs. For the diagnostic magnetic resonance examination 112, image data are acquired that exhibit a significantly higher spatial resolution than the spatial resolution of the image data of the second image data record.

Although modifications and changes may be suggested by those skilled in the art, it is the intention of the inventors to embody within the patent warranted hereon all changes and modifications as reasonably and properly come within the scope of their contribution to the art.

The invention claimed is:

1. A method to acquire magnetic resonance (MR) diagnostic image data from a treatment region, comprising at least one layer, of a patient, comprising:
   (a) operating an MR data acquisition unit, comprising a movable patient bed on which the patient is situated in the MR data acquisition unit, to acquire a first image data set from the patient with a first spatial resolution;
   (b) providing said first image data set to a computerized processor and, in said computerized processor, reconstructing a first image from the first image data set;
   (c) in said computerized processor, automatically determining, from said first image, whether the patient is erroneously situated on said patient bed so as to require manual repositioning of the patient on the patient bed and, if so, emitting error information at a display in communication with said computerized processor that prompts manual repositioning of the patient on the patient bed;
   (d) in said computerized processor, also automatically determining, from said first image, whether said treatment region deviates from a central examination region of said MR data acquisition unit and, if so, automatically shifting said patient bed;
   (e) repeating (a), (b), (c) and (d) until said computerized processor determines that said patient is not erroneously situated on said patient bed and that said treatment region does not deviate from said central examination region based on said first image;
   (f) operating said MR data acquisition unit to acquire a second image data set from the patient with a second spatial resolution that is higher than said first spatial resolution;
   (g) providing said second image data set to said computerized processor and, in said computerized processor, reconstructing a second image from the second image data set;
   (h) in said computerized processor, determining, from said second image, whether said treatment region deviates from said central examination region of said MR data acquisition unit and, if so, automatically shifting said patient bed;
   (i) repeating (f), (g) and (h) until said computerized processor determines that there is no deviation of said treatment region from said central examination region of said MR data acquisition unit based on said second image;
   (j) in said computerized processor, automatically executing a layer planning, dependent on said second image, for acquiring diagnostic MR data from said at least one layer of the patient; and
   (k) from said computerized processor, operating said MR data acquisition unit according to said layer planning to acquire said diagnostic MR data from said at least one layer of the patient in the MR data acquisition unit.

2. A method as claimed in claim 1 comprising acquiring said diagnostic image data from said at least one layer with a third spatial resolution that is higher than said second spatial resolution.

3. A magnetic resonance (MR) apparatus for acquiring image data from a treatment region, comprising at least one layer, of a patient, comprising:
   an MR data acquisition unit comprising a central treatment region, and comprising a movable patient bed on which the patient is situated in the MR data acquisition unit;
   a control computer and a display in communication with said control computer, said control computer being configured to:
      (a) operate said MR data acquisition unit to acquire a first image data set from the patient with a first spatial resolution;
      (b) reconstruct a first image from the first image data set;
      (c) automatically determine, from said first image, whether the patient is erroneously situated on said patient bed so as to require manual repositioning of the patient on the patient bed and, if so, emit error information at said display that prompts manual repositioning of the patient on the patient bed;
      (d) also automatically determine, from said first image, whether said treatment region deviates from a central examination region of said MR data acquisition unit and, if so, automatically shift said patient bed;
      (e) repeat (a), (b), (c) and (d) until said control computer determines that said patient is not erroneously situated on said patient bed and that said treatment region does not deviate from said central examination region based on said first image;
(f) operate said MR data acquisition unit to acquire a second image data set from the patient with a second spatial resolution that is higher than said first spatial resolution;
(g) reconstruct a second image from the second image data set;
(h) determine, from said second image, whether said treatment region deviates from said central examination region of said MR data acquisition unit and, if so, automatically shifting said patient bed;
(i) repeat (f), (g) and (h) until said control computer determines that there is no deviation of said treatment region from said central examination region of said MR data acquisition unit based on said second image;
(j) automatically execute a layer planning, dependent on said second image, for acquiring diagnostic MR data from said at least one layer of the patient; and
(k) from said control computer, operate said MR data acquisition unit according to said layer planning to acquire said diagnostic MR data from said at least one layer of the patient in the MR data acquisition unit.

4. An MR apparatus as claimed in claim 3 wherein said control computer is configured to operate said MR data acquisition unit to acquire said diagnostic MR image data from said at least one layer with a third spatial resolution that is higher than said second spatial resolution.

\* \* \* \* \*